United States Patent [19]

Crouch et al.

[11] Patent Number: 4,649,695
[45] Date of Patent: * Mar. 17, 1987

[54] METHOD AND APPARATUS FOR PRODUCING LIQUID IMPREGNATED FABRIC WIPES

[75] Inventors: Bill W. Crouch, Brown Deer; William F. Sauer, Sussex; Kenneth R. Zylka, Grafton, all of Wis.

[73] Assignee: Meridian Industries, Inc., Milwaukee, Wis.

[*] Notice: The portion of the term of this patent subsequent to Oct. 11, 2000 has been disclaimed.

[21] Appl. No.: 468,326

[22] Filed: Feb. 22, 1983

Related U.S. Application Data

[63] Continuation-in-part of Ser. No. 306,169, Sep. 28, 1981, Pat. No. 4,408,437.

[51] Int. Cl.⁴ .............................................. B65B 63/00
[52] U.S. Cl. .................................. 53/431; 53/111 R; 53/252; 53/500; 53/520
[58] Field of Search ..................... 53/431, 111 R, 252, 53/520, 475, 500, 501, 117, 116, 244

[56] References Cited

U.S. PATENT DOCUMENTS

| | | | |
|---|---|---|---|
| 3,286,435 | 11/1966 | Weinberger | 53/431 X |
| 3,291,678 | 12/1966 | Enloe et al. | 53/431 X |
| 3,348,905 | 10/1976 | Reveley | 53/425 X |
| 3,805,474 | 4/1974 | Gerstein | 53/520 X |
| 3,826,058 | 7/1974 | Preisig | 53/475 X |
| 3,973,373 | 8/1976 | Williams, Sr. et al. | 53/520 X |
| 3,978,636 | 9/1976 | Clancy | 53/431 |
| 4,189,896 | 2/1980 | Kolbach et al. | 53/436 X |

Primary Examiner—James F. Coan
Attorney, Agent, or Firm—Andrus, Sceales, Starke & Sawall

[57] ABSTRACT

A method and apparatus for producing liquid impregnated fabric wipes and packaging the wipes in a container. Fabric material in sheet form is initially passed through a folder to fold the side edge of the sheet, and the folded sheet then travels over a pair of liquid impregnating tubes where liquid is discharged from slots in the tubes against opposite faces of the folded sheet material. After impregnation with the liquid, several sheets are placed together in superimposed form and cut into short lengths to form wipes. The wipes are supported along their side edges by two pair of cooperating endless conveyor belts and as the wipes move along the conveyor, a reciprocating platen moves downwardly between the spaced belts to eject the wipes from the belts onto a conveyor or pack the wipes into a container.

24 Claims, 12 Drawing Figures

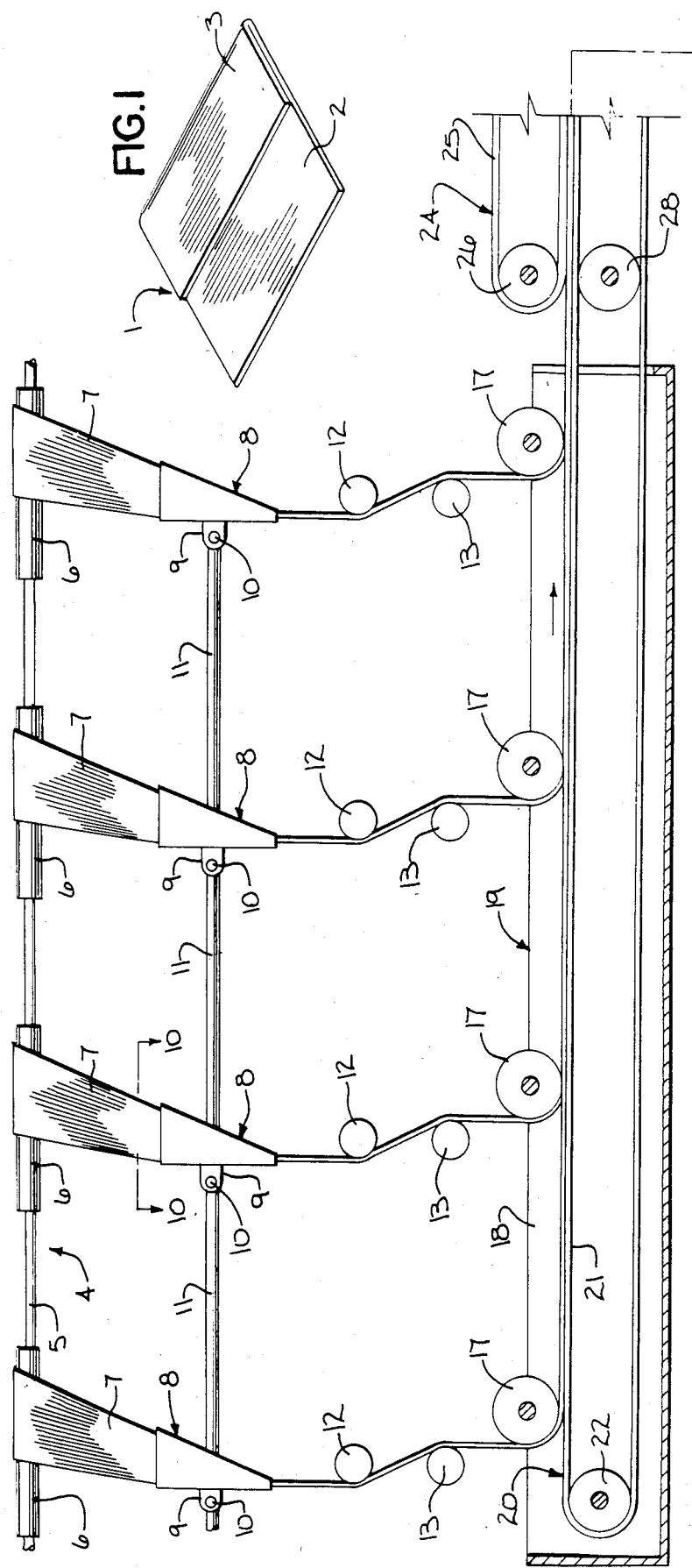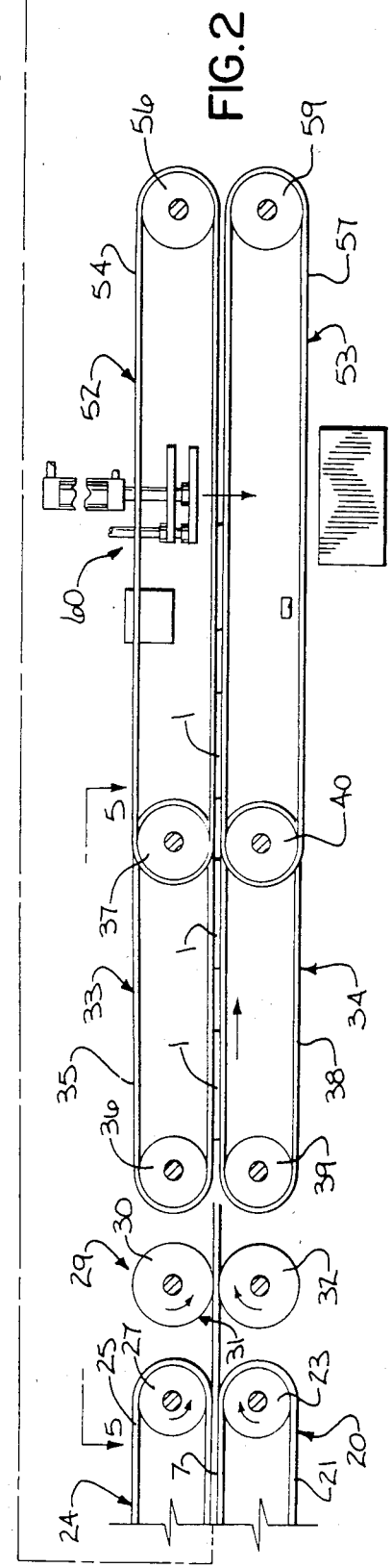

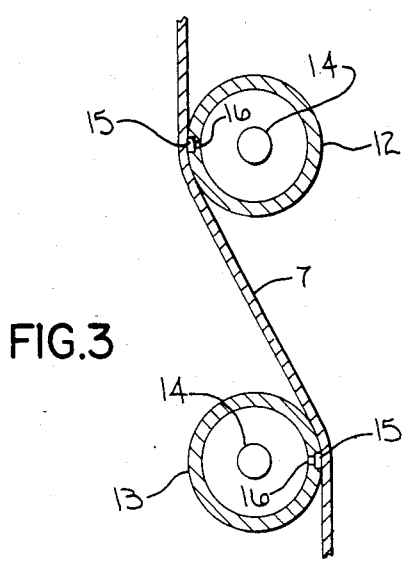
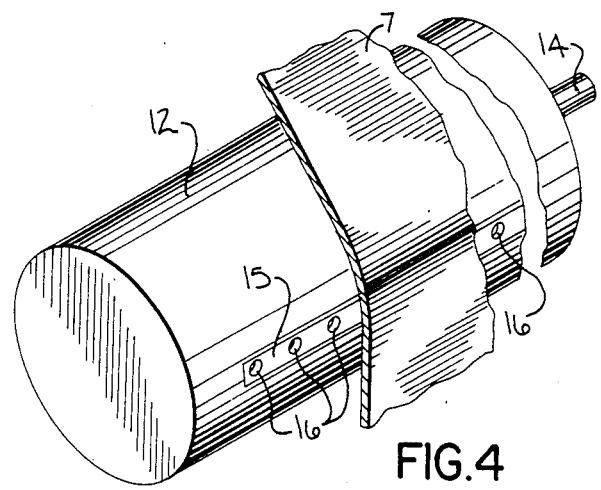
FIG.3
FIG.4
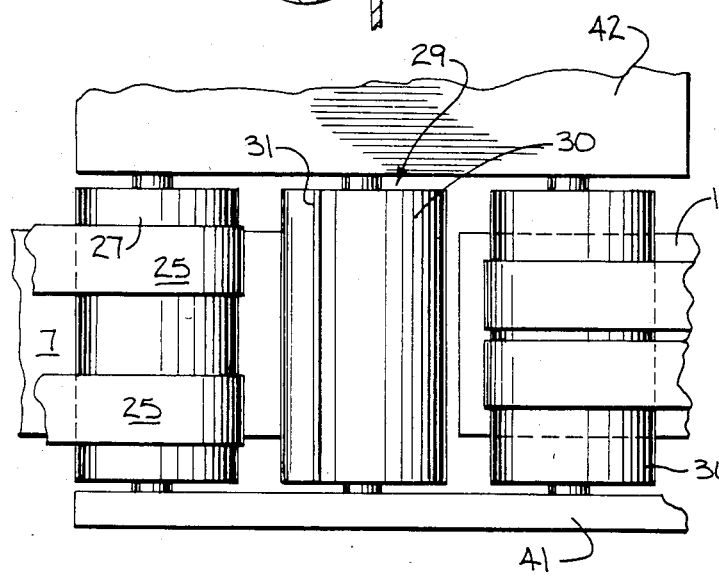
FIG.5
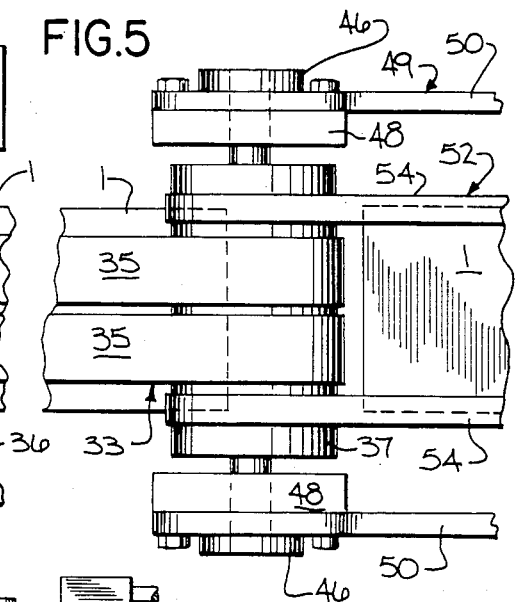
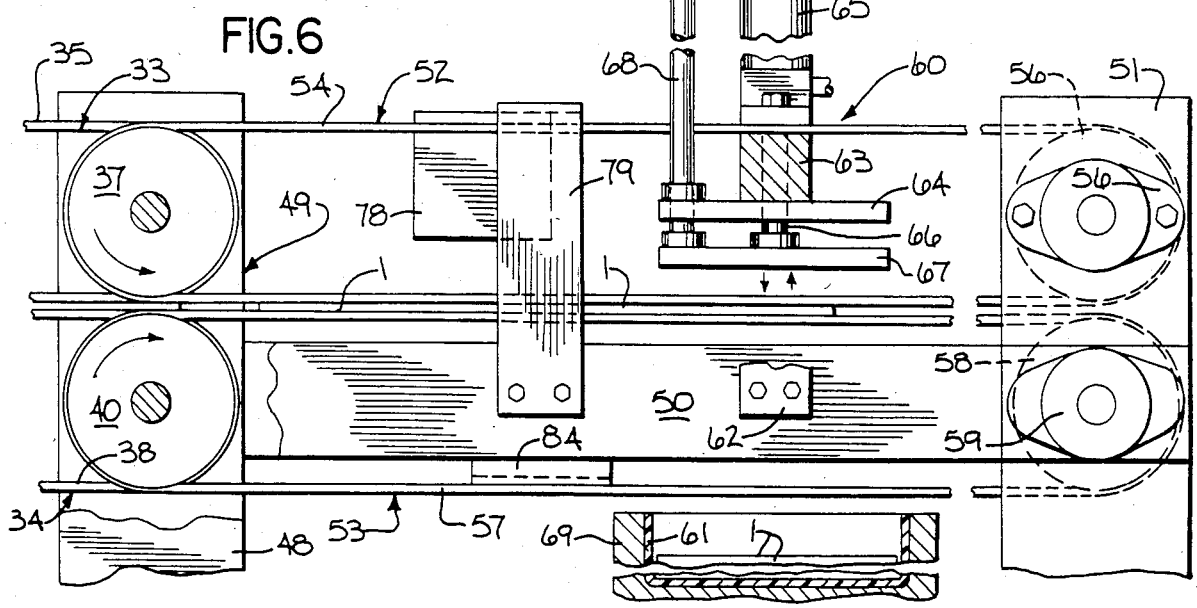
FIG.6

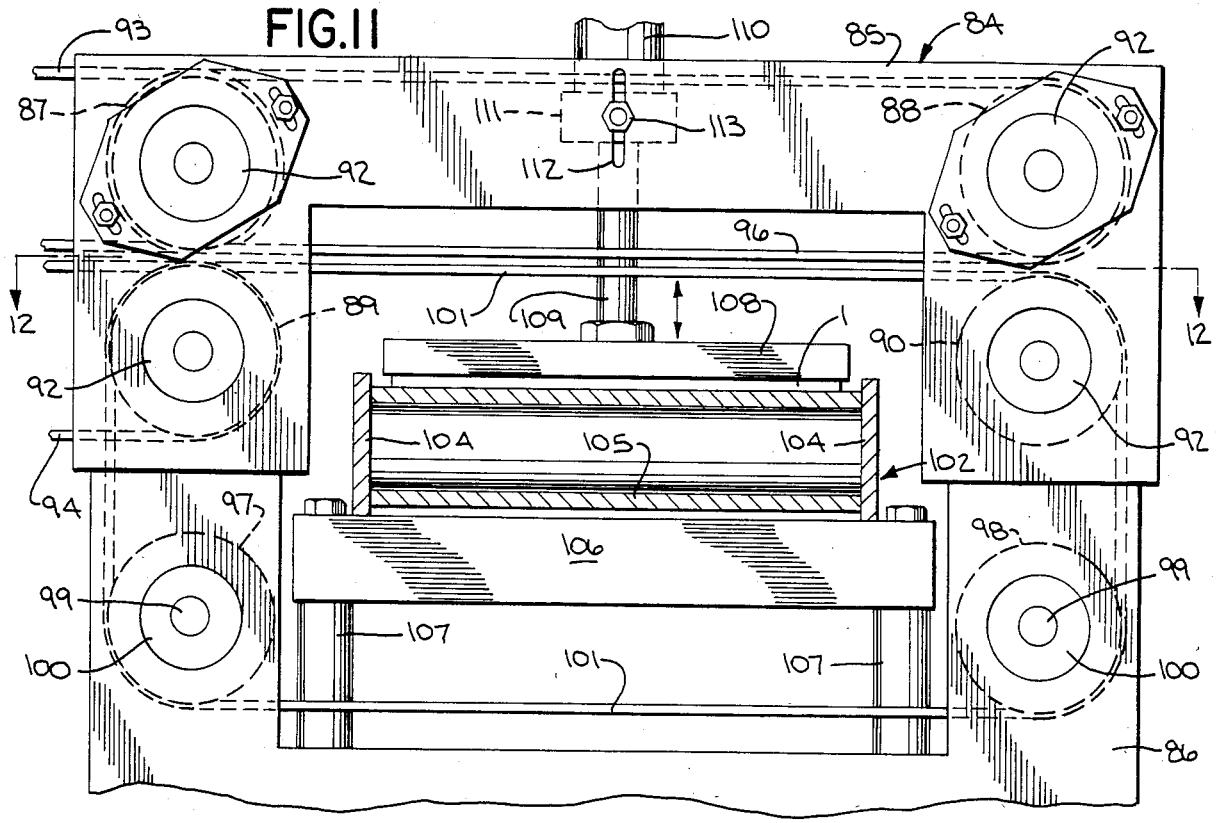

METHOD AND APPARATUS FOR PRODUCING LIQUID IMPREGNATED FABRIC WIPES

RELATED APPLICATION

This application is a continuation-in-part of application Ser. No. 06/306,169, filed Sept. 28, 1981, now U.S. Pat. No. 4,408,437.

BACKGROUND OF THE INVENTION

Body wipes, such as anal wipes, vagina wipes, or hand wipes, are generally formed of tissue paper impregnated with an aqueous solution. The wipes are normally folded and packaged in a hermetically sealed container.

In the past, wipes have been formed in a continuous process by passing the paper tissue through a liquid bath to saturate the tissue and the saturated tissue then passes between pressure rolls to remove the excess liquid. After impregnation, the tissue is passed over vacuum cylinders which support the tissue and the tissue is folded, cut and stacked in a series of sequential operations. However, in the normal manufacturing process the stacked wipes are manually packaged in a container.

The equipment as used in the past to produce wipes has been very expensive and has been custom built for each specific type of product.

SUMMARY OF THE INVENTION

The invention is directed to an improved method and apparatus for producing liquid impregnated fabric wipes and packaging the wipes in a container. In accordance with the process of the invention, the fabric material, such as paper tissue in sheet form, is passed through a folding mechanism to fold a side edge of the sheet. The folded sheet then travels over a pair of impregnating tubes where the liquid impregnant is discharged through slots against opposite faces of the folded sheet to thoroughly impregnate the tissue with the liquid.

After impregnation, several sheets are placed in superimposed form and the superimposed sheets are continuously cut into short lengths to form wipes. The wipes are supported along their side edges by two pair of endless conveyor belts and a reciprocating platen or plunger moves downwardly within the space beteween the conveyor belts to eject the wipes from the belts and pack the wipes into a container.

The plunger which acts to package the wipes in the container, is actuated by a sensing mechanism. When the sensing mechanism senses the presence of a wipe as it moves along the conveyor, the plunger is then actuated to eject the wipe from the spaced conveyor belts and package the wipe into the container.

In addition, a second sensing mechanism counts the number of wipes that are packaged in the container. After a selected number of wipes have been packaged, the filled container is automatically moved from its loading position beneath the conveyor to an unloading position, and a second empty container is simultaneously positioned beneath the container in a loading position to receive the next ejected wipe.

The apparatus of the invention provides a continuous and automatic method of impregnating sheet material with a liquid impregnant, cutting the sheet material into selected lengths to form wipes, and automatically packaging the wipes in a marketing container.

The apparatus employed to impregnate the tissue provides a more uniform application of the liquid than impregnation mechanisms as used in the past.

By packaging the wipes directly into the marketing container, the invention substantially reduces the overall labor cost over prior processes which required manual packaging.

In a modified form of the invention, the wipes instead of being ejected from the spaced conveyor belts by the plunger mechanism into a container, are ejected onto a discharge conveyor. After a predetermined number of wipes are stacked on the discharge conveyor, the discharge conveyor is indexed to remove the stack to a location where they can be packaged in a flexible film package.

Other objects and advantages will appear in the course of the following description.

DESCRIPTION OF THE DRAWINGS

The drawings illustrate the best mode presently contemplated of carrying out the invention.

In the drawings:

FIG. 1 is a perspective view of a wipe as produced by the invention;

FIG. 2 is a side elevation of the apparatus for producing and packaging wipes;

FIG. 3 is an enlarged fragmentary side elevation showing the mechanism for impregnating the sheet material;

FIG. 4 is a perspective view of the mechanism for impregnating the sheet material;

FIG. 5 is an enlarged fragmentary top plan view of the cutting station;

FIG. 6 is an enlarged side elevation of the packaging station;

FIG. 11 is a side elevation of a modified form of the packaging station where the wipes are deposited on a discharge conveyor; and FIG. 12 is a section taken along line 12—12 of FIG. 11.

DESCRIPTION OF THE ILLUSTRATED EMBODIMENT

FIG. 2 shows an apparatus for forming liquid impregnated wipes 1 and packaging the wipes in a marketing container. The wipe, which is produced by the invention, is illustrated in FIG. 1 and includes a main body portion 2 and a folded edge portion 3. When packaged, the folded edge portion 3 of the wipe faces upwardly and can be grasped by the consumer to remove the wipe from the container.

Figure 10:
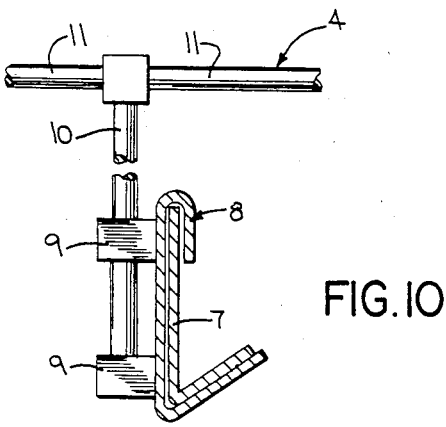
FIG. 10 is a section taken along line 10—10 of FIG. 2 and showing the sheet folding mechanism.

As illustrated in FIG. 2, the apparatus for producing the wipes includes a supporting frame 4 including an upper horizontal rod 5, and a series of rollers 6 are mounted in spaced relation along the length of the rod. Sheets 7 of tissue paper, or other absorbent fabric material, are drawn from suitable supply coils, not shown, and pass over the rollers 6. Each sheet 7 is fed through a folding unit which acts to fold a side edge of the sheet, as best shown in FIG. 10. As shown in FIG. 2, four sheets of tissue 7 are utilized and each sheet is passed through a folding unit 8. The folding units 8 are oppositely oriented so that each alternate sheet will have the opposite side edge folded.

Each of the folding units 8 is provided with a pair of brackets 9 which receive horizontal rods 10, and rods 10, in turn, are connected to the rods 11 of frame 4 which are located beneath the upper rods 5.

After each sheet 7 is folded, the sheet passes over a pair of liquid applicators 12 and 13 which act to apply a liquid impregnant to opposite surfaces of the folded sheet. Each pair of liquid applicators 12 and 13 is connected to a supply manifold 14, which, in turn, is connected to a reservoir or supply for the liquid. The liquid is pumped through the manifold to the liquid applicators 12 and 13.

To provide uniform impregnation, each applicator 12 and 13 is provided with a longitudinally extending slot 15 and the slot communicates with the interior of each applicator through a plurality of spaced holes 16. The outer slot 15 provides uniform distribution of the liquid along the width of the sheet. By proper distribution of the holes 16, the quantity of liquid being distributed along the length of the slot can be varied. Thus, it is possible to distribute a greater quantity of liquid into the folded area of the sheet 7 as opposed to the unfolded area.

After impregnation, each folded sheet 7 passes under a plastic coated roller 17 that is journalled within the side walls 18 of a trough 19. The sheets 7 are then conveyed horizontally on a conveyor 20 which comprises a pair of parallel spaced endless belts 21. Belts 21 are carried by rolls 22 and 23, and roll 22 is journalled in the side walls 18 of the trough 19. As shown in FIG. 2, the folded sheets 7 are disposed in overlapping relation to provide a superimposed array of sheets at the downstream end of the conveyor 20.

As shown in FIG. 2, a second conveyor 24 is located above the downstream end of conveyor 20 and includes a pair of spaced parallel belts 25, which are mounted on the rolls 26 and 27, and are aligned with belts 21. Roll 28 is mounted beneath the roll 26 and carries the spaced belts 21. The superimposed impregnated sheets 7 pass between the cooperating belts 21 and 25 to hold the sheets in proper alignment. The ends of the rolls 26 and 28 are suitably journalled for rotation within the supporting frame 4.

The superimposed sheets 7 are discharged from the cooperating conveyors 20 and 24 to a cutting station 29 where the sheets are cut into lengths to form the wipes 1. The cutting station 29 includes a rotating cutting roll 30 having a longitudinally extending blade 31 that cooperates with a lower roll 32 to cut the sheet into the desired lengths as it passes between the two rolls 30 and 32.

The wipes are then conveyed from the cutting station 29 by a pair of cooperating discharge conveyors 33 and 34. The upper conveyor 33 includes a pair of endless belts 35 which are disposed in side-by-side relation on rolls 36 and 37. Similarly, the lower conveyor 34 includes a pair of belts 38 which are disposed in side-by-side relation and are carried by rolls 39 and 40.

To drive the conveyors 20, 24, 33 and 34, as well as the cutting rolls 30 and 32, the corresponding ends of the shafts of rolls 23, 27, 30, 32, 36 and 39, are journalled within suitable bearings in a housing 41, as illustrated in FIG. 5, while the opposite ends of the roll shafts are operably connected to a gear drive, housed within gear box 42. An electric motor, not shown, is connected in a conventional manner to the input of the gear drive and the gearing is selected to produce the desired speed and direction of rotation for the rolls 23, 27, 30, 32, 36 and 39.

The cutting rolls 30 and 32 operate at the same speed as the delivery conveyors 20 and 24 but the discharge conveyors 33 and 34 operate at a somewhat faster speed in order to remove the cut wipes 1 from the cutting station 29 and to space the wipes along the length of the discharge conveyors 33 and 34.

As shown in FIG. 5, the shafts of the rolls 37 and 40 are journalled within bearings 46 and 47, respectively, which are mounted on vertical supports 48 of frame 49. Frame 49 also includes a pair of spaced horizontal side members 50 which connect the vertical supports 48 with similar vertical supports 51 located at the discharge end of the unit.

The wipes 1 being conveyed between the conveyors 33 and 34 are transferred to conveyors 52 and 53. Conveyor 52 includes a pair of endless belts 54 which are spaced a substantial distance apart. The belts 54 as best shown in FIG. 5, are trained over the roll 37 and are located on either side of the belts 35. The opposite ends of the belts 54 are carried by a roll 55 and the shaft of the roll 55 is journalled within bearings 56 mounted on the supports 51.

The conveyor 53 is similar in construction to conveyor 52 and includes a pair of endless belts 57 which are carried in spaced relation on the roll 40 and located outwardly of the belts 38. The opposite ends of the belts 57 are mounted on roll 58 and the shaft of the roll 58 is journalled within bearings 59 carried by the supports 51. With this construction, the belts 35 and 38 are driven through the drive rolls 36 and 39, and the belts 35 and 38, in turn, drive the rolls 37 and 40 to drive the belts 54 and 57 of conveyors 52 and 53.

To maintain the proper alignment of the various conveyor belts on the respective rolls, the rolls are provided with circumferential grooves which receive ribs on the undersurface of the respective belts.

As previously noted, the cut wipes 1 are transferred from the conveyors 33 and 34 to the conveyors 52 and 53 and are delivered to a packaging station 60 where the wipes are ejected from the conveyor belts 54 and 57 and deposited in a container 61.

Figure 7:
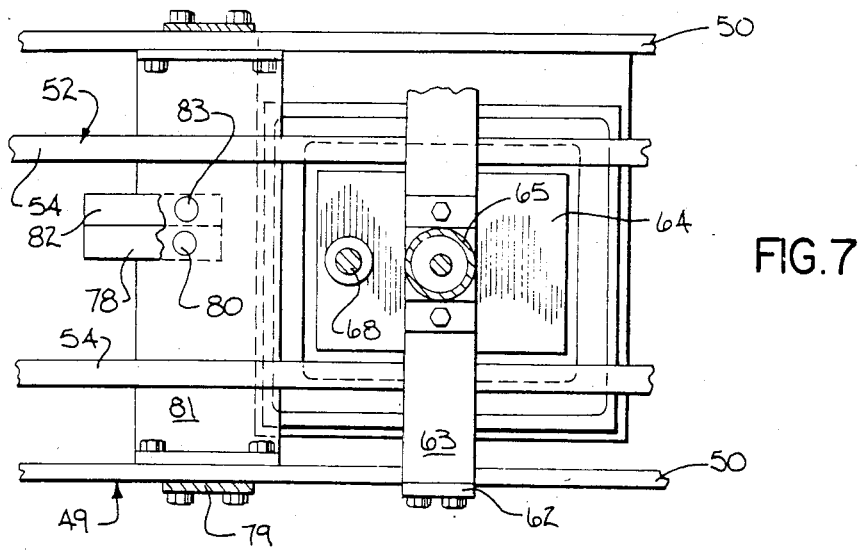
FIG. 7 is a top plan view of the packaging station.

As shown in FIGS. 6 and 7, supports 62 extend upwardly from the horizontal frame members 50 and an elongated block 63 is connected to the upper ends of supports 62 and bridges the conveyors 52 and 53. A fluid cylinder 65 is mounted on the block 63 and a piston or ram 66, which is slidable within the cylinder 65, extends through an opening in block 63 and is connected to a platen 67. The platen 67 has a lateral dimension slightly less than the distance between the belts 54 and 57, and by extending the ram 66, the platen 67 will move downwardly between the spaced belts 54 and 57 to discharge the wipes 1 from the belts and deposit the wipes into the hinged container 61.

To prevent rotation of the platen 67 and maintain its proper relationship with the spaced belts 54 and 57, a guide rod 68 extends upwardly from the edge of the platen 67 and is mounted for sliding movement within a bushing mounted on plate 64. Alternately, a ram or piston rod of non-circular configuration can be used to maintain proper alignment of the platen 67.

Hinged container 61 is supported within fixtures 69 and 70 which are mounted in laterally spaced relation on a reciprocating table or platform 71. The containers 61 are adapted to be moved from a loading position, in vertical alignment with the platen 67, to an unloading position spaced laterally of the conveyors 52 and 53 where the filled container 61 can be removed from the respective fixture and an empty container installed.

Figure 8:
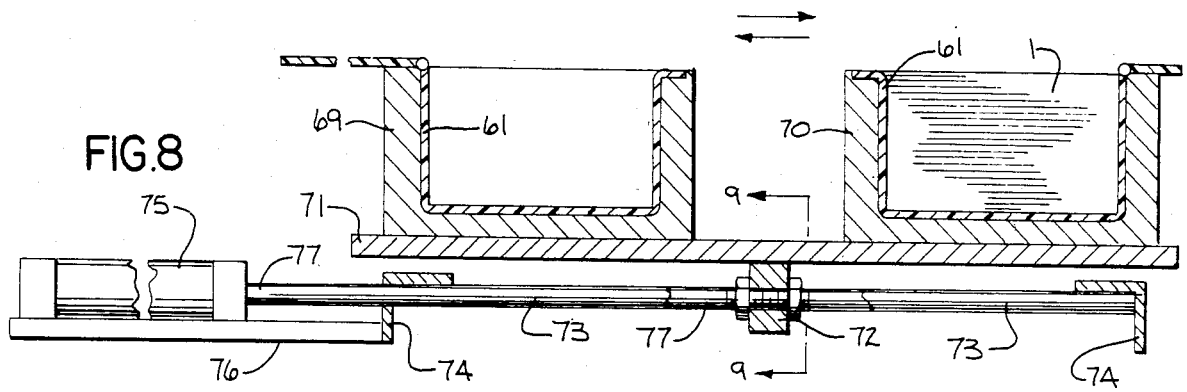
FIG. 8 is a vertical section of the reciprocating table which supports the packaging containers.
Figure 9:
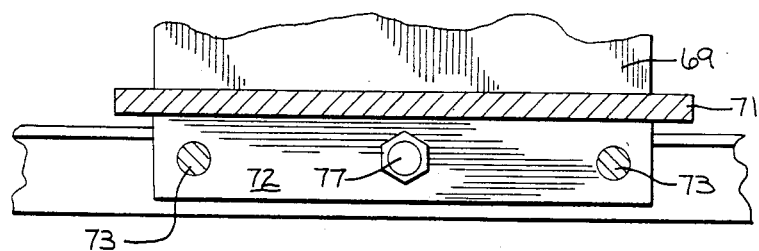
FIG. 9 is a section taken along line 9—9 of FIG. 8.

To reciprocate the table 71, a bracket 72 is mounted centrally on the undersurface of the table and the bracket is slidable on a pair of fixed parallel guide rods 73. As best shown in FIG. 8, the guide rods 73 are secured to a pair of angle irons 74 which are mounted on frame 49, on opposite sides of the lower conveyor 53. A fluid cylinder 75 is mounted on an extension plate 76 connected to one of the angles 74 and the piston rod or ram 77 of the cylinder 75 extends through a suitable opening in one of the angle irons 74 and is connected to bracket 72. Engagement of the depending bracket 72 with the respective flanges of the angle 74 limits the movement of the table in both directions.

As previously noted, the cylinder acts to move the container 61 from a loading position, in alignment with the platen 67, to an unloading position. While one container 61 is being filled with wipes at the loading position, a second filled container can be removed from the fixture at the unloading position and replaced with an empty container.

A sensing mechanism is utilized to operate the platen 67 and deliver the wipes 1 into the container 61. In this regard, a photoelectric eye 78 is mounted on the central portion of a U-shaped bracket 79 which is connected to the horizontal frame members 50 and bridges the conveyors 52 and 53. A sensor 80 is mounted in vertical alignment with the photoelectric eye on a cross member 81 which is connected between the frame members 50. The light beam from the photoelectric eye 78 will be interrupted by the wipes 1 as they are moved by the conveyors 52 and 53, and the interruption of the light beam operates to transmit a signal to the fluid cylinder 65 to extend the platen 67 and move the wipe downwardly into the container 61.

A second sensing mechanism is utilized to operate the reciprocating table 71. This sensing mechanism includes a photoelectric eye 82 mounted in tandem with the photoelectric eye 78, and the photoelectric eye 82 is mounted in vertical alignment with a sensor 83 carried by the cross member 80, as shown in FIG. 7. Sensor 83 is operably connected to a counter and interruptions of the light beam are counted and when a predetermined number of counts have been made, the cylinder 75 is operated to move the reciprocating table 71 and move the filled container 61 to the unloading position and move an empty container to the loading position or station. The filled container 61 is then removed from the fixture and the hinged cover is closed to seal the wipes within the container.

FIGS. 11-12 illustrate a modified form of the packaging station in which the wipes are deposited onto a discharge conveyor instead of being deposited into a container as illustrated in FIGS. 1-10. The packaging station, as illustrated in FIGS. 11-12 comprises a frame or supporting structure 84 composed of inverted U-shaped side members 85 and a pair of U-shaped base members 86 which support the respective side members.

A series of rollers 87-90 are mounted between the side members 85. As illustrated in FIG. 12, the shaft 91 of each roller extends through the respective side members 85 and is journalled within bearing blocks 92 mounted on the outer surface of side members 85. The upper bearing blocks 92 on each side can be mounted for adjustable movement on the side members 85 to adjust the relative vertical position of rollers 87 and 88 with respect to the corresponding rollers 89 and 90.

Drive belts 93, corresponding to drive belts 35 of the first embodiment, are carried by the upper roll 87, while drive belts 94 are carried by the lower roller 89. Belts 93 and 94 are mounted within shallow grooves 95 formed in the periphery of the respective rolls.

The upper rollers 87 and 88 are connected by a pair of belts 96 corresponding to belts 54 of the first embodiment.

A pair of rollers 97 and 98 are journalled between the upper ends of the base members 86. The shafts 99 of rollers 97 and 98 extend through openings in the respective base members 86 and are journalled within bearing blocks 100 which are mounted on the outer surface of the base members. A pair of belts 101 are trained over the rollers 89, 90, 98 and 97 and are located in vertical alignment with the belts 95. Belts 101 also ride within shallow grooves in the roller. The wipes 1 are conveyed between the cooperating belts 96 and 101 as described in the first embodiment.

In accordance with the construction shown in FIGS. 11-12, the wipes 1 are ejected from the conveying belts 96 and 101 onto a transversely disposed discharge conveyor 102, which is located beneath the upper run of the belts 101. As shown in FIG. 11, the discharge conveyor 102 includes an endless conveyor belt 103 which is carried by a drive roll and an idler roll, not shown. Belt 103 travels between a pair of spaced vertical side walls 104 which are connected at their lower edges by a base 105. Conveyor 102 is supported by transversely extending support bar 106, which is mounted on a pair of posts 107 that extend upwardly from the central portion of the base members 86.

The wipes 101 being conveyed by the belts 96 and 101 are ejected downwardly onto the conveyor 102 by a pusher mechanism similar to that previously described in the first embodiment. The pusher mechanism includes a generally horizontal platen 108 which is connected to the lower end of a piston rod 109 that is carried by a piston slidable within cylinder 110. As shown in FIG. 11, the cylinder 110 is mounted on plate 111 that extends laterally between the side members 85 of frame 84.

In order to adjust the lowermost position of the stroke of the platen 108, the plate 111 is adjustably mounted with respect to the side members 85. In this regard, the side members 85 are provided with elongated slots 112 and adjusting studs 113 extend through the slots and are threaded into the plate 111. By loosening the studs, the plate can be moved vertically relative to the frame 84 to thereby adjust the stroke of the platen 108.

To guide the platen in vertical movement a guide rod 114 is connected to the platen and extends through an opening in the plate 111.

Platen 108 is provided with a pair of vent openings 115 and as the platen is lowered to push the wipes downwardly onto conveyor 102, the air will be vented upwardly through the platen.

A sensing mechanism, not shown, similar to that shown by photoelectric eye 78 and sensor 79, is mounted on the frame 84 and acts to operate the platen 108 and deliver the wipes 1 onto conveyor 102, as previously described. In addition, a second sensing mechanism, not shown, such as that illustrated by photoelectric eye 82 and sensor 83 can be mounted on frame 84 to index the conveyor 102. This sensor is operably connected to a counter and interruptions of the light beam are counted and when a predetermined number of counts have been made, the drive for conveyor 102 is actuated to index the conveyor 102 and move the stack of wipes laterally of the frame 84 to a location where they can be packaged.

The invention provides an improved method and apparatus for impregnating sheet material with a liquid, cutting the sheet material into selected lengths as wipes, and packaging the wipes in a marketing container.

The liquid impregnating system as used in the invention provides a more efficient and uniform application of liquid onto the sheet material, and the automatic packaging of the cut wipes substantially reduces labor costs over prior art methods of manufacturing wipes.

While the above description has indicated that the wipes are body wipes used for hygenic purposes, it is contemplated that the apparatus can be used to produce various types of liquid impregnated materials, such as dusting cloths, polishing cloths, insecticidal wipes, and the like. Thus, the wipes can be formed of any type of absorbent material and the liquid can take the form of aqueous solutions, oils, emulsions, and the like.

Various modes of carrying out the invention are contemplated as being within the scope of the following claims particularly pointing out and distinctly claiming the subject matter which is regarded as the invention.

I claim:

1. An apparatus for producing liquid impregnated wipes, comprising liquid impregnating means for continuously impregnating a sheet of absorbent material with a liquid, cutting means for cutting the impregnated sheet into desired lengths to form a plurality of wipes, conveyor means to convey the wipes from the cutting means, said conveying means including two pair of laterally spaced cooperating members, each pair of members cooperating to engage the respective side edges of the wipes, and ejecting means disposed adjacent the conveyor means and disposed to move downwardly within the space between said cooperative pairs of said members to eject the wipes from the members.

2. The apparatus of claim 1, and including folding means for continuously folding a side edge of the sheet to provide a folded sheet, said folding means being located upstream of said liquid impregnating means.

3. The apparatus of claim 1, wherein said liquid impregnating means includes a pair of liquid dispensing tubes, each tube having a discharge slot, opposite sides of said sheet engaging the respective slots to thereby dispense liquid onto opposite sides of said sheet.

4. The apparatus of claim 3, wherein said tube includes a hollow interior connected to a source of liquid supply, and said tube is provided with a plurality of spaced holes providing communication between said interior and said slot.

5. The apparatus of claim 1, and including means for spacing the apart along said conveyor means whereby said means can operate sequentially to eject each successive wipe from said cooperating members.

6. The apparatus of claim 1, wherein said ejecting means includes a generally flat platen mounted for movement between a retracted position and an extended position, said platen when in the retracted position being located at a level above the wipes being transported by said conveyor means and said platen when in said extended position being disposed at a beneath level the wipes being transported by said conveyor means.

7. The apparatus of claim 1, and including a container disposed in alignment beneath said ejecting means to receive the wipes ejected from said members.

8. The apparatus of claim 7, and including a pair of said containers, a supporting table disposed beneath the level of said conveyor means, a pair of said fixtures mounted on table, one of said containers mounted on each fixture, and means for reciprocating the table laterally of said conveyor means to thereby alternately position each of said containers beneath said ejecting means.

9. The apparatus of claim 1, and including a discharge conveyor disposed in alignment with said ejecting means and located beneath the level of said cooperating members to receive the wipes ejected from said members, said discharge conveyor being movable laterally with respect to said conveyor means to thereby convey the wipes to an exterior location.

10. An apparatus for producing liquid impregnated wipes, comprising liquid impregnating means for continuously impregnating a sheet of absorbent material with a liquid, cutting means for cutting the impregnated sheet into desired lengths to form a plurality of wipes, conveyor means to convey the wipes from the cutting means, said conveying means including two pair of laterally spaced cooperating endless belts, each pair of belts having cooperating runs engaging the respective side edges of the wipes with the central portion of the wipes being free of support, and reciprocating means including a reciprocating member movable between a retracted position wherein said reciprocating member is located above said conveyor means to an extended position located beneath said conveyor means, said reciprocating member being disposed in vertical alignment with the space between said belts, and wipe receiving means located beneath said cooperating runs in alignment with said reciprocating member whereby movement of said reciprocating member from the retracted position to the extended position will push a wipe from said belts and deposit the wipe onto said wipe receiving means.

11. The apparatus of claim 10, wherein said liquid impregnating means includes a pair of generally parallel spaced tubes with each tube being connected to a source of liquid, each tube having a discharge slot extending longitudinally of the tube, said slots being disposed transverse to the direction of movement of said sheet and being arranged so that the liquid will be distributed through each slot onto opposite surfaces of said sheet.

12. The apparatus of claim 11, wherein each tube includes a hollow interior connected to said source of liquid and each tube is provided with a plurality of spaced holes providing communication between said interior and the respective slot.

13. The apparatus of claim 10, and including a delivery conveyor located upstream of said cutting means for delivering the sheet to said cutting means, said conveyor means operating at a faster speed than said delivery conveyor whereby the wipes will be spaced along the length of said conveyor means.

14. The apparatus of claim 10, wherein said reciprocating member comprises a generally flat platen, said platen having a lateral dimension slightly less than the distance between said spaced belts, whereby the platen can move to said extended position between said belts.

15. The apparatus of claim 10, and including means located upstream of said reciprocating means and responsive to the presence of a wipe on said conveyor means for operating said reciprocating member to push said wipe from said belts onto said wipe receiving means.

16. The apparatus of claim 10, and including a table disposed beneath said conveyor means and mounted for reciprocating movement in a direction transverse to the movement of conveyor means, a pair of said fixtures mounted on said table with each fixture adapted to support a container, second reciprocating means to reciprocate said table in said transverse direction whereby each container is alternately moved between a loading position disposed in alignment with said reciprocating member to an unloading position disposed laterally of said conveyor means, and means responsive to a given number of wipes being loaded into a first of said containers at said loading position for operating said second reciprocating means to move said first container to the unloading position and to correspondingly move a second of said containers from the unloading position to the loading position.

17. The apparatus of claim 14, wherein said platen has an air vent opening extending therethrough.

18. An apparatus for producing liquid impregnated wipes, comprising liquid impregnating means for continuously impregnating a sheet of absorbent material with a liquid, cutting means for cutting the impregnated sheet into desired lengths to form a plurality of wipes, conveyor means to convey the wipes from the cutting means, said conveying means including a pair of laterally spaced endless conveyor belts, each belt having a conveying run to support the respective side edges of the wipes, with the central portion of said wipes being free of support, wipe receiving means disposed in alignment with the space between said space d belts and located at a level beneath said conveying runs, and wipe ejecting means disposed above said conveying runs and located in alignment with said wipe receiving means for exerting a downward force on the wipes to eject the wipes from said belts and move said wipes to said wipe receiving means.

19. The apparatus of claim 18, and including sensing means for sensing the presence of a wipe on said conveyor belts and operably connected to said wipe ejecting means for actuating said wipe ejecting means and moving said wipe to said wipe receiving means.

20. The apparatus of claim 18, and including means for moving said wipe receiving means in a direction laterally of said conveyor means, and counting means for counting a predetermined number of wipes delivered to said wipe receiving means for operating said wipe receiving means and moving said wipes to a location laterally of said conveyor means.

21. A method of producing liquid impregnated wipes, comprising the steps of impregnating a sheet of absorbent material with a liquid, cutting the impregnated sheet into desired lengths to form a plurality of wipes, supporting each wipe along its side edges by a pair of spaced supports while transporting the wipes in a path of travel, and pushing each individual wipe from the spaced supports by exerting a force against said wipe in alignment with the space between said supports, and delivering said wipe to a wipe receiving means.

22. The method of claim 21, and including the step of continuously folding a side edge of the sheet to produce a folded sheet prior to impregnating said sheet with said liquid.

23. A method of producing liquid impregnated wipes, comprising the steps of continuously impregnating a sheet of absorbent material with a liquid, cutting the impregnated sheet into desired lengths to form a plurality of wipes, transporting the wipes by engaging the side edges of each wipe between two cooperating pairs of spaced moving endless belts while maintaining the central portion of each wipe unsupported, and moving a plunger downwardly within the space between said pairs of cooperating belts to thereby eject the wipes from engagement with said belts and deposit said wipes onto a wipe receiving means.

24. The method of claim 23, and including the step of spacing said wipes longitudinally along said belts.

* * * * *

UNITED STATES PATENT AND TRADEMARK OFFICE
CERTIFICATE OF CORRECTION

PATENT NO. : 4,649,695

DATED : March 17, 1987

INVENTOR(S) : Bill W. Crouch et al.

It is certified that error appears in the above-identified patent and that said Letters Patent is hereby corrected as shown below:

Claim 5, line 59, after "the" insert -- wipes --.

Claim 6, lines 68 and 1, delete "beneath level" and substitute therefor -- level beneath --.

Claim 8, line 8, before "fixtures" cansel "said".

Signed and Sealed this

Twelfth Day of April, 1988

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,649,695

DATED : March 17, 1987

INVENTOR(S) : BILL W. CROUCH ET AL

It is certified that error appears in the above-identified patent and that said Letters Patent is hereby corrected as shown below:

CLAIM 5, Line 59, After "the" insert ---wipes---; CLAIM 5, Line 60, After "said" insert--- ejecting--.

Signed and Sealed this

Sixteenth Day of August, 1988

Attest:

DONALD J. QUIGG

*Attesting Officer*     *Commissioner of Patents and Trademarks*